US010761093B2

(12) United States Patent
Pappas

(10) Patent No.: US 10,761,093 B2
(45) Date of Patent: Sep. 1, 2020

(54) MICRODEVICE FOR CELL SEPARATION UTILIZING ACTIVATION PHENOTYPE

(71) Applicant: TEXAS TECH UNIVERSITY SYSTEM, Lubbock, TX (US)

(72) Inventor: Dimitri Pappas, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 424 days.

(21) Appl. No.: 15/517,921

(22) PCT Filed: Oct. 9, 2015

(86) PCT No.: PCT/US2015/054979
§ 371 (c)(1),
(2) Date: Apr. 7, 2017

(87) PCT Pub. No.: WO2016/057945
PCT Pub. Date: Apr. 14, 2016

(65) Prior Publication Data
US 2017/0307611 A1  Oct. 26, 2017

Related U.S. Application Data

(60) Provisional application No. 62/061,739, filed on Oct. 9, 2014.

(51) Int. Cl.
*G01N 33/569* (2006.01)
*G01N 33/543* (2006.01)
(Continued)

(52) U.S. Cl.
CPC .... *G01N 33/56972* (2013.01); *B01L 3/50273* (2013.01); *G01N 33/54366* (2013.01);
(Continued)

(58) Field of Classification Search
CPC ....... G01N 33/56972; G01N 33/54366; G01N 33/569; G01N 33/00; B01L 3/50273; C12Q 1/00
See application file for complete search history.

(56) References Cited

U.S. PATENT DOCUMENTS 5,804,370 A   9/1998  Romaschin
7,645,573 B2  1/2010  Ivey
(Continued)

FOREIGN PATENT DOCUMENTS

WO   WO2004/029221   4/2004
WO   WO2006/061644   6/2006

OTHER PUBLICATIONS

Sethu et al. Microfluidic Isolation of Leucocytes from Whole Blood for Phenotype and Gene Expression Analysis. Ana. Chem. 78: 5452-5461 (2006).*

(Continued)

*Primary Examiner* — Gailene Gabel
(74) *Attorney, Agent, or Firm* — Dickinson Wright PLLC; Kristopher Lance Anderson

(57) ABSTRACT

Disclosed is a system and method for a microdevice to separate blood cells based on differences in antigen expression. Specifically, cells of the same phenotype are separated based on whether or not they are activated during infection or resting. The device of the present disclosure takes a small sample of blood and provides differential cell counts that can be used to test for infection and inflammatory response. The device can be used to identify sepsis and other infections rapidly. By measuring differences in activated white cell counts such as neutrophils, the device of the present disclosure measures physiological response to infection in hospitalized patients recovering from burns, surgeries, etc.

6 Claims, 13 Drawing Sheets

(51) Int. Cl.
    *B01L 3/00*     (2006.01)
    *C12Q 1/00*     (2006.01)
    *G01N 33/00*     (2006.01)

(52) U.S. Cl.
    CPC .............. *G01N 33/569* (2013.01); *C12Q 1/00* (2013.01); *G01N 33/00* (2013.01)

(56) References Cited

U.S. PATENT DOCUMENTS

| | | | |
|---|---|---|---|
| 7,767,395 B2 | 8/2010 | Garrett | |
| 8,304,230 B2 * | 11/2012 | Toner | B01L 3/502746 435/288.5 |
| 8,439,835 B1 | 5/2013 | McKinley | |
| 8,476,028 B2 | 7/2013 | Toner | |
| 8,518,648 B2 | 8/2013 | Bjorck | |
| 8,669,113 B2 | 3/2014 | Shi | |
| 8,986,988 B2 * | 3/2015 | Karnik | C12N 5/0068 435/325 |
| 2008/0114576 A1 | 5/2008 | Jackson | |
| 2011/0059858 A1 | 3/2011 | Kas | |

OTHER PUBLICATIONS

"Microfluidic Antibody Arrays for Simultaneous Cell Separation and Stimulus"; Anal Bioanal Chem (2014) 406; 7867-7873; 8 pages.
"Cellular Separations: A Review of New Challenges in Analytical Chemistry"; Analytica Chimica Acta, Nov. 2007; 12 pages.
"Continuous Flow Microfluidic Device for Cell Separation, Cell Lysis and DNA Purification"; Analytical Chimica Acta 584 (2007) 237-243; 8 pages.
"Microfluidic Isolation of Leukocytes from Whole Blood for Phenotype and Gene Expression Analysis"; Analytical Chemistry, vol. 78, No. 15, Aug. 1, 2006, 5453-5461; 9 pages.
International Preliminary Report on Patentability for related International Patent Application No. PCT/US2015/054979 dated Apr. 11, 2017; 10 pages.
International Search Report for International Patent Application No. PCT/US2015/0564979 dated Dec. 22, 2015; 16 pages.

* cited by examiner

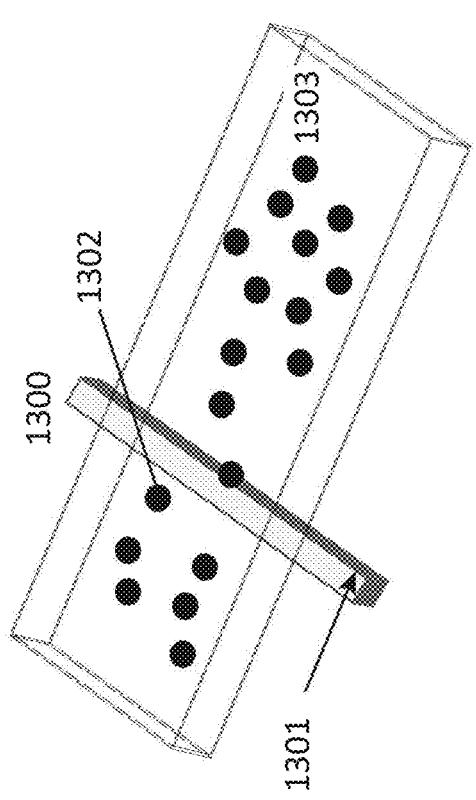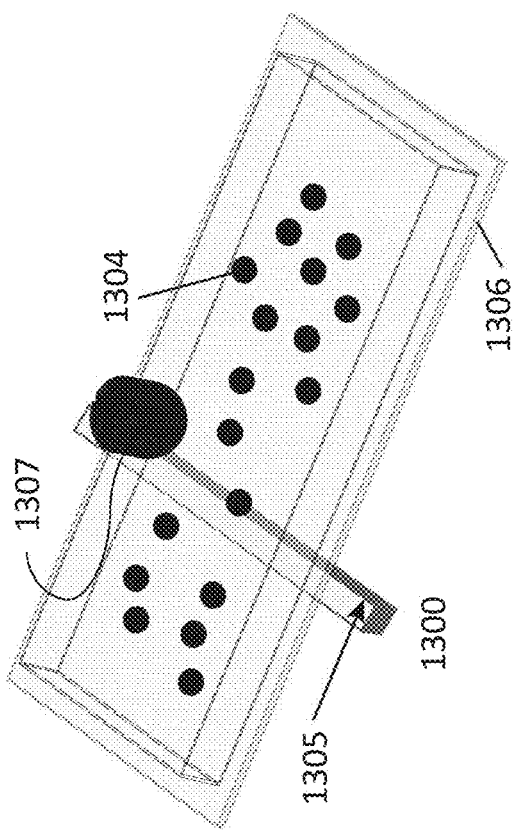
FIG. 13A
FIG. 13B

MICRODEVICE FOR CELL SEPARATION UTILIZING ACTIVATION PHENOTYPE

CROSS-REFERENCE TO RELATED APPLICATIONS

This application is a national phase filing of PCT/US2015/054979, filed on Oct. 9. 2015, entitled "Microdevice For Cell Separation Utilizing Activation Phenotype" which claims priority to provisional U.S. Patent Application Ser. No. 62/061,739, filed on Oct. 9, 2014, entitled "Microdevice for Cell Separation Utilizing Activation Phenotype" which provisional patent application is commonly assigned to the Assignee of the present invention and is hereby incorporated herein by reference in its entirety for all purposes.

This application includes material that is subject to copyright protection. The copyright owner has no objection to the facsimile reproduction by anyone of the patent disclosure, as it appears in the Patent and Trademark Office files or records, but otherwise reserves all copyright rights whatsoever.

TECHNICAL FIELD

The present disclosure relates in general to the field of diagnosis and detection of biological samples. In particular, the system provides for a microdevice to separate blood cells based on differences in antigen expression. The disclosed systems and methods support a wide variety of scenarios and includes various products and services. Examples of end-use applications include the detection of sepsis, isolation of activated neutrophil cells, and the detection of proliferating cells from resting cells.

STATEMENT OF FEDERALLY FUNDED RESEARCH

None.

BACKGROUND OF THE DISCLOSURE

Infection is defined as the invasion of a host organism's body tissues by disease-causing agents, their multiplication, and the reaction of host tissues to these organisms and the toxins they produce. Infectious diseases, also known as transmissible diseases or communicable diseases, comprise clinically evident illness (i.e., characteristic medical signs and/or symptoms of disease) resulting from the infection, presence and growth of pathogenic biological agents in an individual host organism.

Infections are caused by infectious agents such as viruses, viroids, and prions, microorganisms such as bacteria, nematodes such as roundworms and pinworms, arthropods such as ticks, mites, fleas, and lice, fungi such as ringworm, and other macroparasites such as tapeworms.

Hosts can fight infections using their immune system. Mammalian hosts react to infections with an innate response, often involving inflammation, followed by an adaptive response.

Sepsis is a potentially fatal whole-body inflammation (a systemic inflammatory response syndrome or SIRS) caused by severe infection. Sepsis is caused by the immune system's response to a serious infection, most commonly bacteria, but also fungi, viruses, and parasites in the blood, urinary tract, lungs, skin, or other tissues. Sepsis can also be caused by toxins even when no identifiable bacteria are present. Sepsis can be thought of as falling within a continuum from infection to multiple organ dysfunction syndrome.

Documenting the presence of the pathogenic microorganisms that are clinically significant to sepsis has proven difficult. Causative microorganisms typically are detected by culturing a subject's blood, sputum, urine, wound secretion, in-dwelling line catheter surfaces, etc. Causative microorganisms, however, may reside only in certain body microenvironments such that the particular material that is cultured may not contain the contaminating microorganisms. Detection may be complicated further by low numbers of microorganisms at the site of infection. Low numbers of pathogens in blood present a particular problem for diagnosing sepsis by culturing blood. In one study, for example, positive culture results were obtained in only 17% of subjects presenting clinical manifestations of sepsis (Rangel-Frausto et al., 1995, JAMA 273:117-123). Diagnosis can be further complicated by contamination of samples by non-pathogenic microorganisms.

Common symptoms of sepsis include those related to a specific infection, but usually accompanied by high fevers, hot, flushed skin, elevated heart rate, hyperventilation, altered mental status, swelling, and low blood pressure. In the very young and elderly, or in people with weakened immune systems, the pattern of symptoms may be atypical, with hypothermia and without an easily localizable infection.

In addition to symptoms related to the provoking infection, sepsis is frequently associated with fever or hypothermia, rapid breathing, elevated heart rate, confusion, and edema. Early signs are elevated heart rate, decreased urination, and elevated blood sugar, while signs of established sepsis are confusion, metabolic acidosis with compensatory respiratory alkalosis (which can manifest as faster breathing), low blood pressure, decreased systemic vascular resistance, higher cardiac output, and dysfunctions of blood coagulation.

Prompt diagnosis is crucial to the management of sepsis, as initiation of early-goal-directed therapy is key to reducing mortality from severe sepsis. Within the first three hours of suspected sepsis, diagnostic studies should include measurement of serum lactate, obtaining appropriate cultures before initiation of antimicrobial treatment, so long as this does not delay antimicrobial treatment by more than 45 minutes. To identify the causative organism(s), at least two sets of blood cultures (aerobic and anaerobic bottles) should be obtained, with at least one drawn percutaneously and one drawn through each vascular access device (such as an IV catheter) in place more than 48 hours. If other sources are suspected, cultures of these sources, such as urine, cerebrospinal fluid, wounds, or respiratory secretions, should be obtained as well, so long as this does not delay antimicrobial treatment.

Within six hours, if there is persistent hypotension despite initial fluid resuscitation of 30 ml/kg, or if initial lactate is ≥4 mmol/L (36 mg/dL), central venous pressure and central venous oxygen saturation should be measured. Lactate should be re-measured if the initial lactate was elevated.

Within twelve hours, it is essential to diagnose or exclude any source of infection that would require emergent source control, such as necrotizing soft tissue infection, peritonitis, cholangitis, intestinal infarction. Sepsis may also lead to a drop in blood pressure, resulting in shock. This may result in light-headedness. Bruising or intense bleeding may also occur. The aforementioned, gross parameters have not been identified as specific to sepsis.

Sepsis is usually treated with intravenous fluids and antibiotics. If fluid replacement is not sufficient to maintain blood pressure, vasopressors can be used. Mechanical ventilation and dialysis may be needed to support the function of the lungs and kidneys, respectively. To guide therapy, a central venous catheter and an arterial catheter may be placed; measurement of other hemodynamic variables (such as cardiac output, mixed venous oxygen saturation or stroke volume variation) may also be used.

Infections cause millions of deaths globally each year. Sepsis and other infections are usually characterized by blood culture, which takes 24-48 hours to identify. Currently, the mortality rate for sepsis is high due to this long waiting period.

Identifying sepsis and other infections earlier can increase survival rates by over 10 times. However, there are still limitations for current detection methods and devices.

SUMMARY OF THE DISCLOSURE

The present disclosure addresses failings in the art by providing a system and method for rapid detection of infections, such as sepsis.

The present disclosure provides for a microdevice to separate blood cells based on differences in antigen expression. Specifically, cells of the same phenotype are separated based on whether or not they are activated during infection or resting. The device of the present disclosure takes a small sample of blood and provides differential cell counts that can be used to test for infection and inflammatory response. The device can be used to identify sepsis and other infections rapidly (less than 12 hours and as low as 6 hours). By measuring differences in activated white cell counts such as neutrophils, the device of the present disclosure measures physiological response to infection in hospitalized patients recovering from burns, surgeries, etc.

The present disclosure identifies sepsis as soon as six hours after infection, allowing physicians to directly measure the body's response to infection. Such information allows physicians and other care providers to respond rapidly to patients with massive inflammatory response to an infection, and thus decrease mortality. The device of the present disclosure may be further implemented in any clinical setting due to its ease of use and low cost. The device of the present disclosure achieves 97-99% accuracy for cell identification in tested blood cell separation from control samples.

It is an object of the present disclosure to provide differential cell counts in a short-time span in order to reduce patient mortality in the detection and/or diagnosis of certain infections.

It is a further object of the present disclosure to provide for the measurement of physiological response to infections in patients. Patients may range from those experiencing acute symptoms of infection to those recovering from burns or surgeries, or other post-incidental infection management and control.

It is a further object of the present disclosure to allow for the quick identification of infections, particularly sepsis (a condition in which timely diagnosis is of the essence). In some embodiments, the system of the present disclosure may be implementable in any clinical setting due to ease of use and low cost. The technology can be utilized to measure differential cell counts of blood. Further, the present disclosure provides for a diagnostic test for infections and inflammations utilizing a microfluidic device of varying arrangements to separate and measure the presence of activated cells, such as neutrophils.

It is yet another object of the present invention to provide a microfluidic detection chip for the detection of infection in a patient comprising: a plurality of layers in which are disposed a plurality of channels; a sample input channel into which a sample fluid mixture of components to be isolated is inputted; one or more separation channels having one or more three-dimensional (3D) separation zones; and one or more channels having one or more optical zones. The one or more 3D separation zones further comprise at least one vertical interface and at least one horizontal interface. The chip may further comprise a separation channel for monocyte depletion. The one or more separation channels may be arranged serially or in parallel. In one aspect, the one or more separation channels comprises an affinity surface comprising a biotinylated antibody, such as anti-CD4, anti-CD19 and the like. The chip may conform to known chip configurations, and may be at least three layers. The separation channels may further comprise a first affinity surface and a second affinity surface for capturing varying levels of expressive cells, such as high-expression neutrophils in a first affinity surface, and a second affinity surface which captures resting neutrophils. Further, the one or more separation channels may comprise a first affinity surface and a second affinity surface arranged in series or in parallel channels. Once captured, it is an object of the present invention to provide enumeration of cells by cell imaging, which may occur by flatbed scanning, which may further comprise using contrasting agents.

It is another object of the present invention to provide a method of identifying the presence of infection, comprising: flowing a patient sample through a microfluidic device having a substrate having formed therein one or more separation channels, at least one portion of the one or more separation channels having a plurality of monolayers, wherein at least a portion of said monolayers comprises a monocyte affinity surface capable of cell capture, and one or more optical zones having a plurality of monolayers, wherein at least a portion of said monolayers comprises a neutrophil affinity surface capable of cell capture; capturing active neutrophils in at least one separation channel; capturing resting neutrophils in at least one separation channel; enumerating the active and resting neutrophils in the optical zone; and determining the ratio of active-to-resting neutrophils. The method may further include depleting monocytes from the sample in the separation channels prior to neutrophil capture. The plurality of separation channels may have more than one monocyte affinity surfaces capable of cell capture of more than one monocytes and may further comprise 3D channels.

In one aspect, the monocyte affinity surface comprises a biotinylated antibody. In addition, the neutrophil affinity surface comprises at least one surface having a biotinylated antibody. In another aspect, the method includes enumerating the active and resting neutrophils using an optical scanner. The optical scanner may be a flatbed scanner and may further utilize a high-contrast dye in bright field. Fluorescence scanning is also possible with the present invention.

It is an object of the present invention to provide separation design that results in enhanced cell capture in affinity microchannels. This high capture efficiency and capture purity allows for removal of unwanted cells from a sample (negative selection) before isolated target cells (positive election). The affinity chips can isolate cell types that cannot be isolated in a single-step analysis. In addition, methods are provided to remove monocytes prior to analysis, a requirement for accurate CD64+ neutrophil counting. A further aspect is to use a single chip to isolate neutrophils based solely on whether they are resting (low CD64 expression) or active (high CD64 expression).

In accordance with one or more embodiments, a system is provided that comprises one or more microfluidic devices configured to provide functionality in accordance with such embodiments. In accordance with one or more embodiments, functionality is embodied in steps of a method performed by at least one computing device. In accordance with one or more embodiments, program code to implement functionality in accordance with one or more such embodiments is embodied in, by and/or on a computer-readable medium particularly with cell enumeration.

BRIEF DESCRIPTION OF THE DRAWINGS

The foregoing and other objects, features, and advantages of the disclosure will be apparent from the following description of embodiments as illustrated in the accompanying drawings, in which reference characters refer to the same parts throughout the various views. The drawings are not necessarily to scale, emphasis instead being placed upon illustrating principles of the disclosure:

FIGS. 13A-B depicts optimized optical scanning configurations for On-Chip readouts.

DETAILED DESCRIPTION OF THE DISCLOSURE

Figure 1:
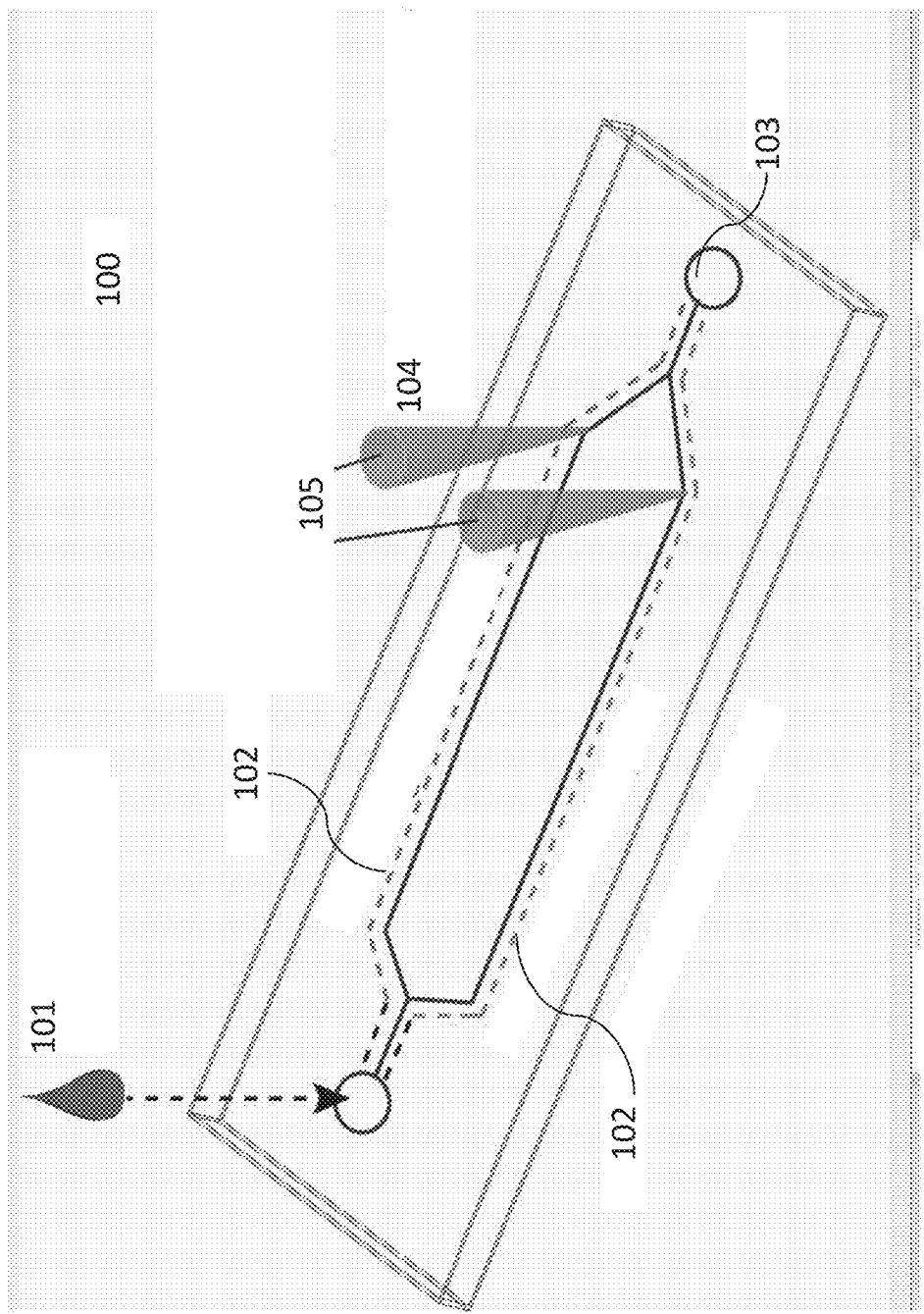
FIG. 1 depicts a microfluidic schematic, in parallel configuration, for measuring the presence of levels of CD64 bodies within a blood sample.

While the making and using of various embodiments of the present disclosure are discussed in detail below, it should be appreciated that the present disclosure provides many applicable inventive concepts that can be embodied in a wide variety of specific contexts, goods, or services. The specific embodiments discussed herein are merely illustrative of specific ways to make and use the disclosure and do not delimit the scope of the disclosure.

All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

The present disclosure will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, devices, components, or systems. Accordingly, embodiments may, for example, take the form of hardware, software, firmware or any combination thereof (other than software per se). The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

The development towards lab-on-a-chip devices has been greatly advanced since the first introduction of microfluidics for chemical analysis, with much progress being made in the area of chemical separations. The attractiveness of microfluidics-based separations to analytical chemists owes to its ability to routinely perform rapid and sensitive experiments on a small footprint with minimal use of sample and reagents. Additionally, microfluidic technology facilitates the fabrication of devices with integrated functions an advantage which has led to a multitude of microdevices for pertinent biochemical assays. The success of microchips in basic research has led to the birth of specialized commercial devices for multiple bioanalytical applications, including applications in cell biology, genetics, pharmacology, and other biomedical fields.

Sepsis, systemic inflammatory response syndrome (SIRS), and septic shock represent significant causes of hospitalization and death in the United States. Sepsis is the 10th highest cause of death with an associated healthcare cost of 16.7 billion dollars. Sepsis-related hospitalizations are 75% longer than patients treated for other conditions. In addition, the percentage of hospitalizations with sepsis-related principle diagnoses has increased from 11.6% in 2000 to 24.0% in 2008. Currently, sepsis is assayed using blood culture or other devices that detect the presence of bacteria. The timeline for detecting sepsis in this manner ranges from 24-48 hours. These blood culture methods do not detect sepsis or septic shock in cases where there are no detectable bacteria.

Sepsis and septic shock continue to be major problems in the treatment of burn and surgery patients. The diagnosis of sepsis typically requires blood culture, which can take 24-48 hours. The long analysis time required for blood culture increases the likelihood of mortality. Alternatively, the physiological responses associated with sepsis can be used as a diagnostic tool. It is known in the art that neutrophil activation is particularly attractive as a quantification of sepsis, since some forms of sepsis have no detectable bacterial infection. Activation of neutrophils during sepsis and SIRS can be measured via changes in CD64 expression and are detectable as early as 3-6 hours after infection. Neutrophil activation is typically measured using fluorescence activated cell sorters and magnetic activated cell sorters; however, they are not readily implemented in every medical setting. For a sepsis assay that can be translated to point of care settings, a simpler, automated approach is needed. Microfluidic methods based on affinity cell chromatography can be adopted in research and clinical settings with minimal cost and infrastructure. While many approaches have been developed for cell separations, most methods isolate cells in a single separation step. Activated and resting neutrophils have differing levels of the same surface marker, making separating these two cell types and quantifying them difficult.

Separating and sorting cells from a heterogeneous mixture is a fundamental step in basic biological, chemical, and clinical studies. In sepsis, a blood culture is typically conducted, requiring several days before a positive result is obtained. Procalcitonin is also used to assay sepsis. However, procalcitonin is also present at elevated levels in other diseases such as malaria and community-acquired pneumonia. However, it is possible to assay the biological response to sepsis, looking for neutrophil activation and subsequent increase in CD64 expression. Cell separations can be used for a rapid assay of sepsis, enumerating activated CD64+ neutrophils from 0.1 mL blood samples in a simple measurement. Cell separations are typically performed using cell sorters or magnetic beads, although other approaches such as dielectrophoresis, magnetophoresis, filtration, and affinity methods have been developed. Most cell isolation methods use one or more different antigens for cell enrichment. However, in neutrophil isolation two groups of cells are isolated—resting and activated neutrophils—that share the same antigens, although they express them at different levels. The key challenge therefore is to separate high- and low-expressing CD64+ neutrophils from each other and from other blood types. The present invention utilizes a chip with different regions of cell capture efficiency to isolate activated and resting neutrophils. Separating cells based on differences in antigen expression requires differences in flow geometries, surface chemistry, or other factors. A chip that can measure differences in neutrophil activation further enables clinicians to identify systemic response to injury or infection, and would aid in sepsis treatment. In addition, automating the analysis and enumeration of cell capture could lead to point of care systems for sepsis assay—a critical need for burn or surgery patients.

It is therefore an embodiment of the present invention to provide cell separation microfluidic chips for analysis of neutrophil activation. These devices will be developed toward producing simple, inexpensive, and rapid tests for CD64+ neutrophil activation counts for point of care sepsis assays. The present invention measures neutrophil activation using affinity cell separations in a microfluidic format and is further able to measure resting and activated neutrophils from small samples of blood. In one embodiment, affinity regions with different CD64+ cell capture efficiencies will differentially isolate resting and activated neutrophils, and that those cells can be enumerated for rapid and inexpensive sepsis assays. These assays are capable of detecting changes in CD64 expression in neutrophils within 3-6 hours of sepsis or SIRS, which is 3-8 times earlier than bacterial assays, wherein the measurement of resting and activated neutrophils is allowed.

The present invention provides for separation systems that use a unique flow architecture to achieve high-efficiency cell separations. The system utilizes three-dimensional (3D configurations, such as herringbone structures for efficient cell capture. This approach allows for increased cell-antibody interaction on the chip surface. In addition, the approach is easy to fabricate and is amenable to optical scanning using simple instrumentation. Each 3D flow interface increases cell capture. Resting and activated neutrophils can be separated using either parallel channels or using serial affinity regions in the same channel. In one embodiment of the present invention, there are two serial affinity regions, each corresponding to cell capture for active or resting neutrophils. A serial affinity design eliminates differences in flow between microfluidic channels and can be used to isolate different cell types from blood. In both series and parallel chips, an anti-CD64 affinity region with low capture affinity will let resting neutrophils pass while capturing activated neutrophils having higher expression of CD64. A second anti-CD64 affinity region with high capture affinity will then capture resting neutrophils. The entire chip is then scanned on a flatbed scanner and cell counting is performed automatically in software to provide the ratio of activated and resting neutrophils.

Cell separations take advantage of physical differences between cells such as size and density, or differences between antigen expression on the cell surface. Dielectrophoresis, sedimentation, and filtration approaches have been developed to isolate cells based on differences in physical properties. In many applications where cell separations are necessary, differences in physical parameters alone are not sufficient to isolate the desired cell type with high purity. Approaches that exploit differences in antigen expression or other affinity-type interactions include fluorescence activated cell sorting (FACS), microfluidics FACS, magnetic activated cell sorting, and affinity methods. However, affinity separations, including FACS, cannot easily isolate cells when more than one cell type expresses the antigen that is recognized by the affinity ligand. It is possible to use multiple affinity tags in FACS, but the cost and complexity of existing instruments preclude point of care diagnosis in most cases. Microfluidic methods for separating similar cell types have not separated identical cell types with different antigen expression levels.

Sepsis, SIRS, and septic shock are traditionally diagnosed initially with gross symptoms such as low blood pressure, elevated heart rate (>90/min), elevated respiratory rate (>20/min), elevated or decreased white cell count (>12,000 or <4,000 cells/mm3), and fever (>38° C.). These methods have a wide degree of variability and can be subjective. Sepsis is then further diagnosed using blood culture although newer methods have been developed to detect bacterial contamination in blood. These approaches still require sufficient time for bacterial levels to rise to their respective detection limits. Typical detection times are 24-48 hours after infection, which coincides with the typical mortality rate for patients with septic shock. The present invention detects physical response to infection, which manifests itself more rapidly. Procalcitonin assays are typically measured after 24 hours, making them less suitable for early detection of sepsis.

The present invention utilizes multiple separation zones are used under both positive and negative selection to isolate cells that cannot easily be separated by other methods. Unlike 96-well formats, the chips of the present invention isolate cells of interest based on affinity separation, followed by whole-chip scanning for enumeration. Negative selection affinity regions can remove interfering cells prior to analysis by positive selection. For example, monocytes (which express CD64) may interfere with neutrophil enumeration. It therefore an object of the present invention to deplete monocytes prior to the blood sample reaching the anti-CD64 affinity regions for neutrophil capture. In the serial affinity chip after monocyte depletion, the first affinity zone captures neutrophils with high CD64 expression, thus depleting those cells prior to capture in the second affinity zone. The second affinity zone therefore captures resting neutrophils. In parallel channel chips of the present invention, blood is split between two channels, one that captures all neutrophils with high affinity and one channel that captures activated neutrophils only. Both approaches will be evaluated to determine the best approach for activated neutrophils detection. It is another embodiment of the present invention to provide the incorporation of on-chip enumeration. In an exemplary embodiment, using a flatbed scanner and a contrast dye added to the running buffer cells are imaged. Flatbed scanners have been used for cell imaging in part because of the large field of view as well as the ability to use commercially available, low-cost systems. Readout can occur using fluorescence or contrasting agents. The approach will automatically count cells to further speed up diagnostics. It is an exemplary embodiment to utilize contrasting agents for flatbed scanning using desktop scanners.

The separation chips of the present invention are therefore designed to increase capture efficiency, capture purity, and separation speed. Microfluidic affinity cell separations require efficient cell-surface interactions to retain cells in the separation channel. It is shown that such affinity approach isolates target cells from blood with 97-99% purity, and that cell capture is greatly enhanced when cell-affinity surface interaction increases. It is thus another embodiment of the present invention to provide enhanced capture surfaces for greater interaction between the cells and the capture ligand to enhance capture efficiency and purity. In an exemplary embodiment, a herringbone mixer will increase capture efficiencies higher than extant approaches. The increased capture surface interaction results in high capture efficiencies that approach 100%. The 3D chip approach is therefore utilized to deplete unwanted cells (e.g. monocytes) prior to isolation of neutrophils using imaging-friendly herringbone channels. Using different flow geometries and affinity capture strategies, separation regions are created capable of isolating activated and resting neutrophils, respectively, thus improving capture efficiency over pillar- and herringbone-type separations alone, enabling cell analyses that have been difficult or impossible in the past by providing chip architecture that will use affinity ligands for efficient cell capture for sepsis assay studies.

Neutrophilic granulocytes express their Fcgamma receptor I, also known as the CD64 antigen, predominantly when they are activated. This makes neutrophil CD64 a known biomarker for infection and sepsis. Indeed there is ample literature on the diagnostic utility of neutrophil CD64 in a variety of diseases. IgG responses are crucial in the diagnosis of infections. Assessing their activation in vitro is of fundamental importance, but technically difficult.

CD64 is a type of integral membrane glycoprotein known as an Fc receptor that binds monomeric IgG-type antibodies with high affinity. It is more commonly known as Fc-gamma receptor 1 (FcγRI). After binding IgG, CD64 interacts with an accessory chain known as the common γ chain (γ chain), which possesses an ITAM motif that is necessary for triggering cellular activation. Human CD64 is a high affinity receptor for monomeric human IgG1 and IgG3 which is expressed on macrophages, monocytes, and gamma interferon induced neutrophils. CD64 plays an important role in clearance of immune complexes and in antibody dependent cytoxicity.

In the present invention, CD64 antibodies, having locus BC032634 and known as *Homo sapiens* Fc fragment of IgG, high affinity Ia, receptor (CD64), mRNA (cDNA clone MGC:45021 IMAGE:5248549), complete cds, Accession BC032634, Version BC032634.1 GI:21619685, are utilized in a microfluidic channel capable of contacting detectably the CD64 antibodies specific for CD64 with blood leucocytes in a sample obtained from the subject. The resulting measurable CD64-antibody complex is identified as abnormal expressions, and suggests the presence of infection.

The principles discussed herein may be embodied in many different forms. The preferred embodiments of the present disclosure will now be described where for completeness, reference should be made at least to the Figures.

FIG. 1 shows an exemplary detection chip 100 of the present invention. A sample 101 is introduced into an inlet having one or more channels for separation 102. The sample 101 may be a blood sample ranging from 100-1000 μL. The channels 102 allow for the sample to flow across the channels which are layered with anti-CD64 bodies. This may be controlled by a control valve (not shown) or by drawing via an outlet 103. FIG. 1 shows the application of the present disclosure to the detection and diagnosis of SIRS, or sepsis, wherein a CD64-affinity chip is utilized. The chip, oriented as a parallel chip, utilizes CD64 antibody to distinguish active and resting states of CD64, a known marker. Enumeration of the distinguished active neutrophils and the distinguished resting neutrophils, present an opportunity to calculate and therefore diagnose, sepsis. The enumeration may occur at an optical channel 105, wherein optical enumeration is achieved by scanning using cell counting beams via laser or LED.

Figure 2:
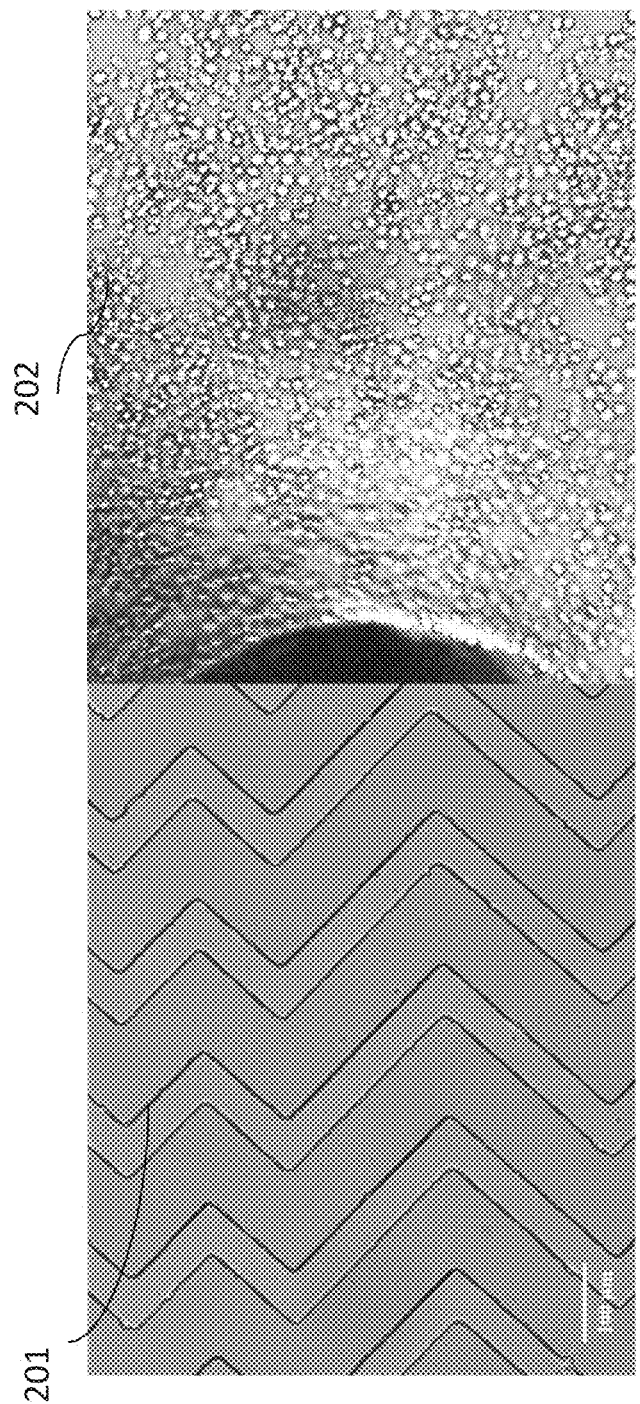
FIG. 2 (A) depicts the three-dimensional (3D) separation channel for negative depletion; and (B) a magnified view of enhanced cell capture of the 3D channels.
Figure 4:
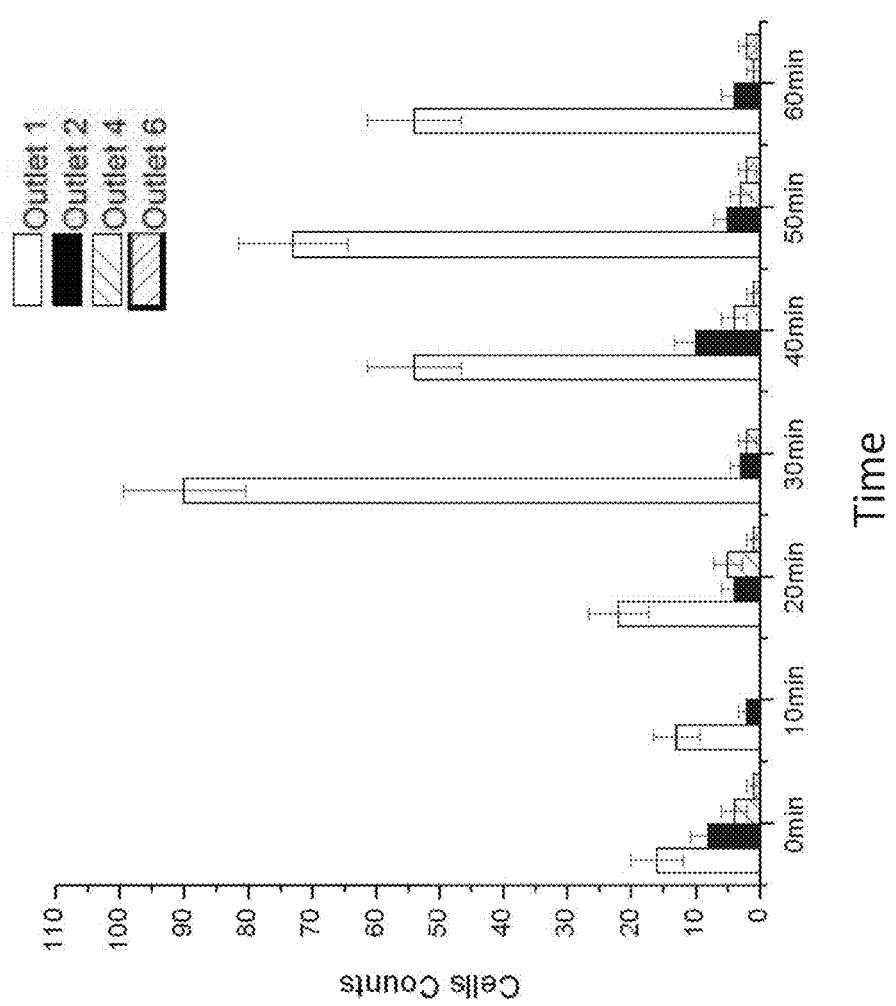
FIG. 4 depicts saturation of the affinity surface as measured by cells passing through the outlet of each 3D stage (y-axis represents cells leaving chip, not retained in channel).

Several approaches have been developed to increase the interaction between cells and the affinity surface. Under most microfluidic conditions, flow is laminar and only cells near the channel surface will interact with affinity ligands. Both micropillars and herringbone mixers have been used to isolate cells either in positive or negative selection modes. However, neither reported approach has been able to achieve high capture efficiencies, which are required for depletion of unwanted cell types for affinity separations. In one embodiment of the present invention, deceleration at the interface between vertical and horizontal channels, a so-called 3D separation stage, increases the interaction time between the cell and the affinity surface. FIG. 2(A) presents an exemplary 3D herringbone configuration 201. Fluorescence correlation spectroscopy (FCS) measurements of single molecules flowing through the chip showed a marked deceleration at each vertical interface, increasing cell retention. The chips reached separation purities of 93%. An exemplary embodiment of the present invention is in the use of multiple 3D stages to overcome the problem of cell surface overloading. The downward trajectory approach to cell separations results in capture efficiencies that overload the affinity surface with cells. As cells occupy the entire capture surface, target cells will pass through the affinity region without being captured. However, in the present invention, each additional 3D stage presents a new affinity surface. As each 3D stage is overloaded sequentially, the remaining stages remain functional to ensure a large number of cells can be captured. FIG. 2(B) provides a more detailed view of a separation 3D channel used for negative depletion before neutrophil capture, which can exceed 98% purity with high capture density 202. In this case CD4+ cells (HuT 78 cell line) were captured with high efficiency. Turning to FIG. 4 it is shown that the number of cells passing through the first 3D stage (Outlet 1) increases after 20 minutes. Saturation of the affinity surface as measured by cells passing through the outlet of each 3D stage (y-axis represents cells leaving chip, not retained in channel). CD4+ HuT 78 cells were depleted from a cell mixture using an anti-CD4 chip with 6 3D interfaces. After 20 minutes, the first 3D affinity surface was completely covered with target cells. At that point, both target and background cells could pass through the channel without capture, degrading separation performance. Using multiple 3D interfaces in our chip ensures that as one affinity surface is saturated, downstream surfaces are available for cell capture. The downward trajectory of a single 3D interface ensures high cell capture, requiring multiple interfaces to avoid saturation. At this point in time the affinity surface was saturated with cells and no additional capture could occur. If only one interface was used, then separation performance would decrease at that time. Using multiple 3D stages increases the total capture capacity. Since the 3D design is not amenable to facile on-chip imaging, this channel type will only be used to isolate unwanted cells to deplete interference cells before CD64 neutrophil capture, which occurs via one or more separation channels.

In early experiments, it was shown that cell capture using the downward trajectory approach was 12 times greater than a straight channel of similar dimensions and linear flow rates. While typical chip designs may have high capture capacity, purity, and efficiency, the latter can be further increased using additional microfluidic structures. In another embodiment, chips are designed with several affinity regions placed in series. These chips deplete and capture one blood cell type in each region, and can be used to isolate leukocytes from blood with high purity (see Table 1). In this case, an anti-CD4 region preceded the anti-CD19 region, and both regions captured their respective cell types with >97% purity. These chips use straight affinity sections referred to herein as separation channels, resulting in a 50-60% capture efficiency. However, both the 3D chip approach and the serial affinity sections can be combined for high purity and high efficiency cell separations.

TABLE 1

Blood Cell Separations Using Affinity-sectioned Chips, Li 2012.

|  | Anti-CD4 Region | Anti-CD19 Region |
|---|---|---|
| Target Cells/mL | 360 ± 40 | 130 ± 70 |
| Total Cells/mL | 370 ± 30 | 130 ± 70 |
| Lot-certified Cells/mL | 707 (CD4+) | 214 (CD19+) |
| Capture Purity (%) | 99.1 ± 0.4 | 97 ± 2 |
| Capture Efficiency (%) | 51 | 61 |
| Li, 2012 | | |

Figure 3:
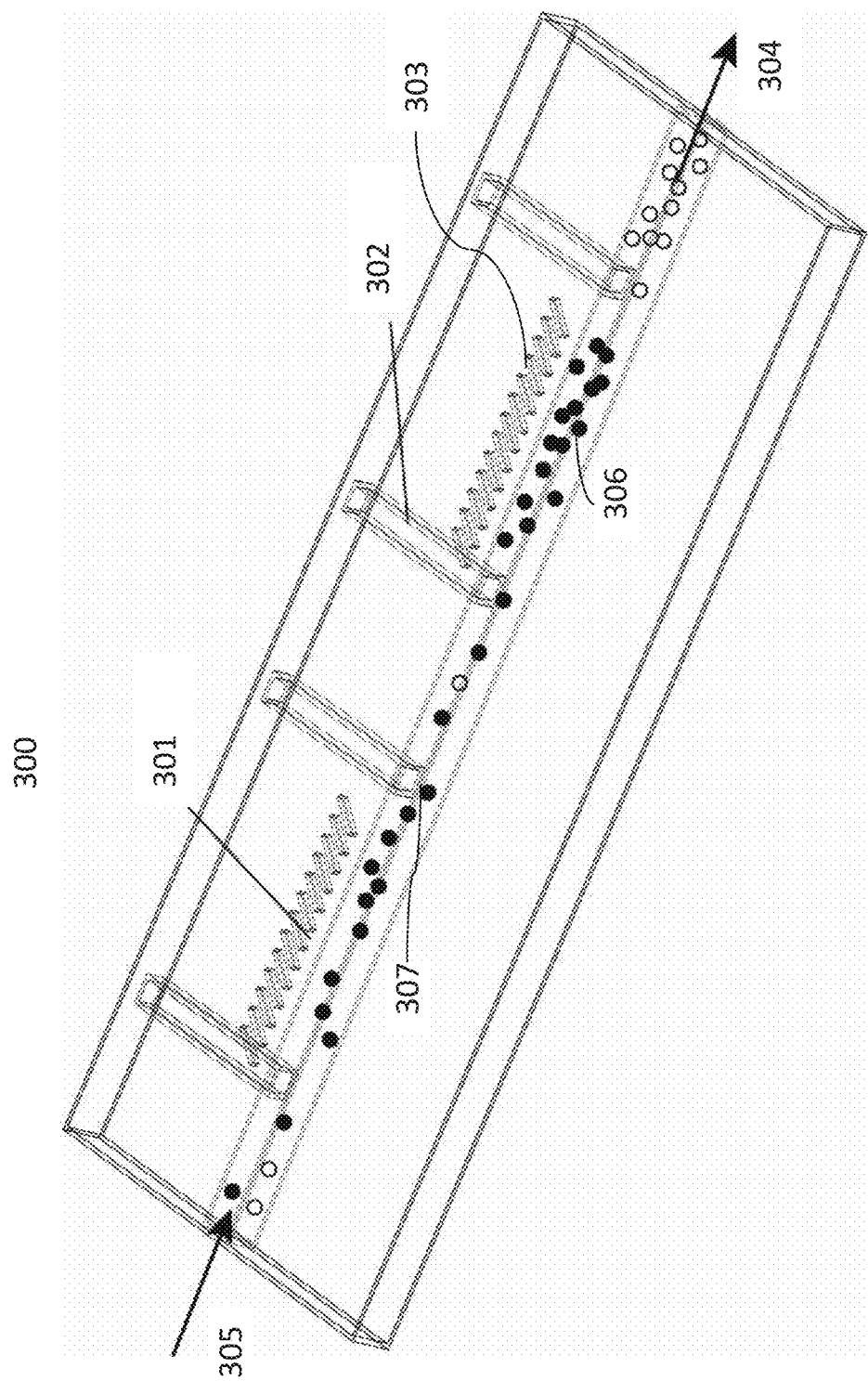
FIG. 3 depicts separation of neutrophils for sepsis assays using a serial channel.

FIG. 3 presents an exemplary embodiment of the principles of the separation channel conveyed herein. Chips 300 are made using poly(dimethylsiloxane) (PDMS) bonded to glass slides. Fluid flow 305 is controlled by syringe pumps or automated means known in the art, and light and fluorescence microscopy is used to assess separations in situ. The chip 300 presents the configuration of separation of neutrophils for sepsis assays using a serial channel. The first separation zone 301 has fewer antibodies on the surface, resulting in lower capture efficiency. Neutrophils showing increased antigen expression are captured in the first separation zone 301 while neutrophils with low antigen expression pass to the second zone 303 and are captured on a high-efficiency capture surface. Flow cytometry verifies cell mixtures before and after separations as a control measurement. A first separation channel 301 contains a low antibody concentration. A second separation channel 303 comprises a high antibody concentration. A control valve is provided 302 for flow modulation if desired. The separation channels 301 and 303 have herringbone channels for providing the 3D interfaces for cell capture of expressing cells 306, 307. Non-expressing cells are then capable of flowing out of the separation channels 301, 303. Separation channels for the purposes of the present invention may also be utilized for monocyte depletion, as well as for concurrent enumeration of the captured cells, which separation channel may be referred to as an optical channel.

The chips of the present invention may be three-layer devices including layers for control lines. The affinity surface can be glass or PDMS. The exemplary designs have a first section with six, repeating 3D interfaces per affinity section for CD14 capture. The dimensions of each interface will first be modeled using COMSOL software to optimize cell-surface interactions. COMSOL further assists in modeling the number of interfaces needed to capture cells with the highest efficiency. Validations of the modeling results occurs using anti-CD71 capture antibodies and Ramos cells to determine the cell capture with the COMSOL-optimized geometries as a starting point.

Figure 5:
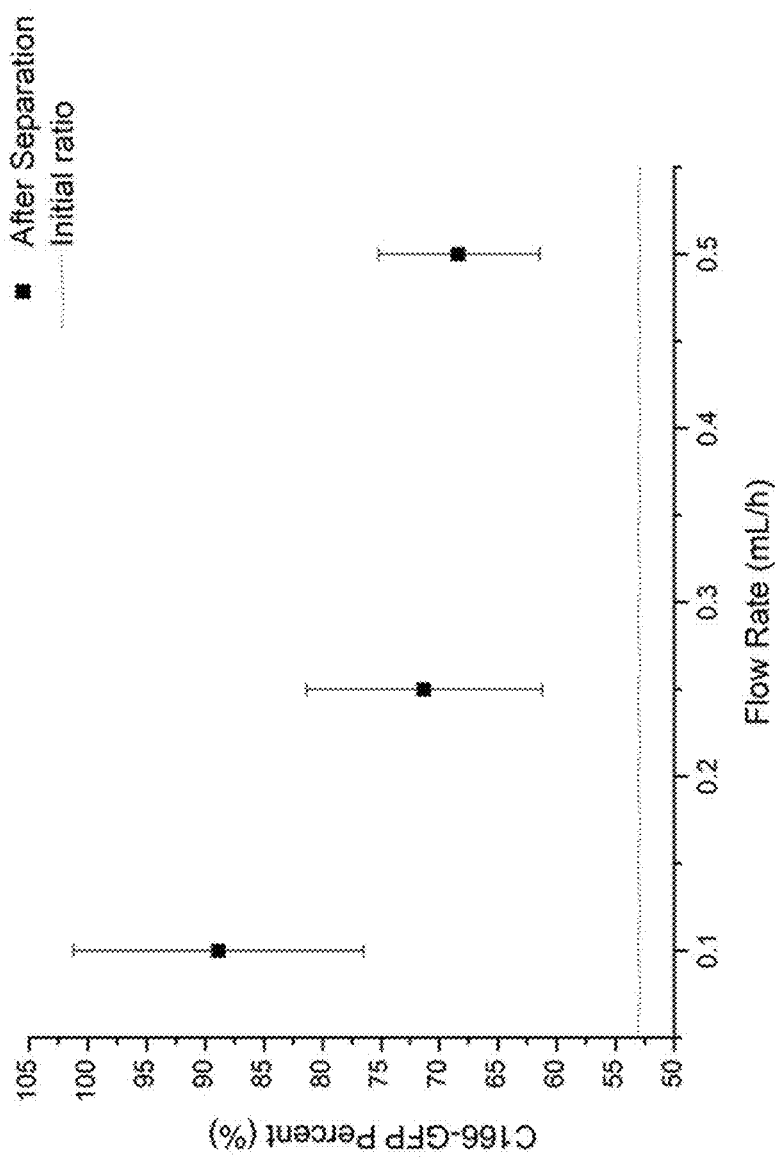
FIG. 5 depicts flow rate effects in cell capture.

Chip-to-chip variability is further determined in cell capture and flow rate. Flow rate may be assessed by visually tracking cell movement through the chip via microscopy. Variations in fabrication can cause changes in the linear flow rate when the same volumetric flow rate is used. In affinity cell separations a cell is captured on the surface if the total affinity adhesion force exceeds the shear force. The number of bonds ($B_c$) needed to retain a cell on the affinity surface can be expressed as $B_c = F/f_c$, where F is the shear force and $f_c$ is the sum of the adhesion force from all affinity bonds between the cell and the surface. The number of bonds formed during a cell-surface interaction (B*) is expressed as:

$$B^* = t_c A_c B_t$$

where B is the density of bonds formed per unit area, $t_c$ is the duration of interaction, and $A_c$ is the contact area between the cell and the affinity surface. Faster flow rates result in less cell capture (see FIG. 5) and the $B*/B_c$ ratio results in cell capture at values >1. This ratio is inversely proportional to the square of the volumetric flow rate. Increasing the volumetric flow rate decreases the cell interaction time, $t_c$, (decreasing B*) and increases the shear force, F (increasing $B_c$). This $1/x^2$ dependence requires careful control of the flow rate. As shown in FIG. 5 there is a rapid drop off in cell purity that approaches the initial concentration ratio of the target cells. Cells were isolated from a mixture by negative selection. The initial ratio of target cells was 53% (dashed line). Slower flow rates resulted in higher separation purity, as background cells were better retained in the chip. To assess flow rate variability between chips, cell suspensions are flowed through the chips at the same volumetric flow rate and measure linear flow rate of cells by video microscopy. Anti-CD19 surfaces are used with Ramos B cells as the target cell. Ramos cells are then mixed with CCRF-CEM cells (which are CD19−) to determine capture purity (Ramos Cells vs. total cells captured), nonspecific binding (CCRF-CEM cells vs. total cells captured) and capture efficiency. To differentiate between the two cell types, Ramos cells are incubated with MitoTracker Green and CCRF-CEM cells with Hoechst 33342 and fluorescence microscopy is then used to count cells. The cell samples and concentrations remain the same for all chip-to-chip variability studies. Captured cells in the chip are measured to determine if the small changes in flow rate affect cell capture. The volumetric flow rates are then adjusted in the same test chips to determine if the same linear flow rate affects differences in cell capture, informing the inter-chip variation in flow and cell capture, and for correcting for differences in flow rate decreases variability.

Figure 6:
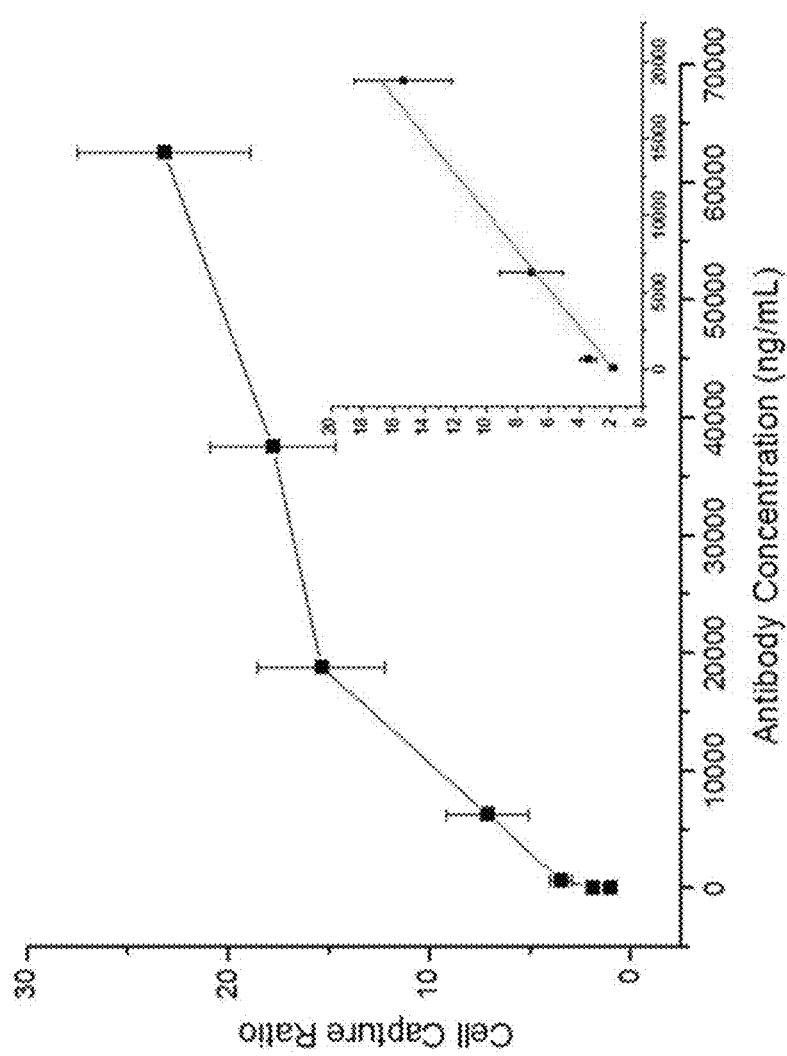
FIG. 6 depicts antibody concentration (loaded into the chip) affects on cell capture.
Figure 7:
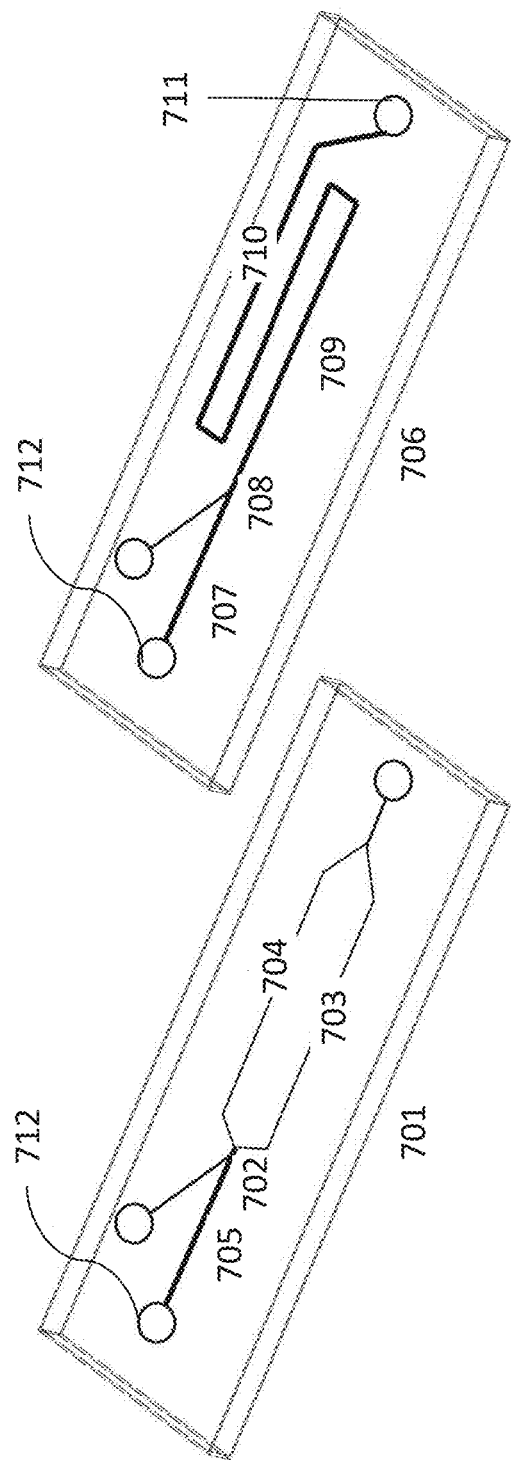
FIG. 7 depicts two embodiments of a microdevice to separate blood cells based on differences in antigen expression (anti-CD64 antibody): (A) comprising a parallel chip orientation; and (B), comprising a series orientation.
Figure 8:
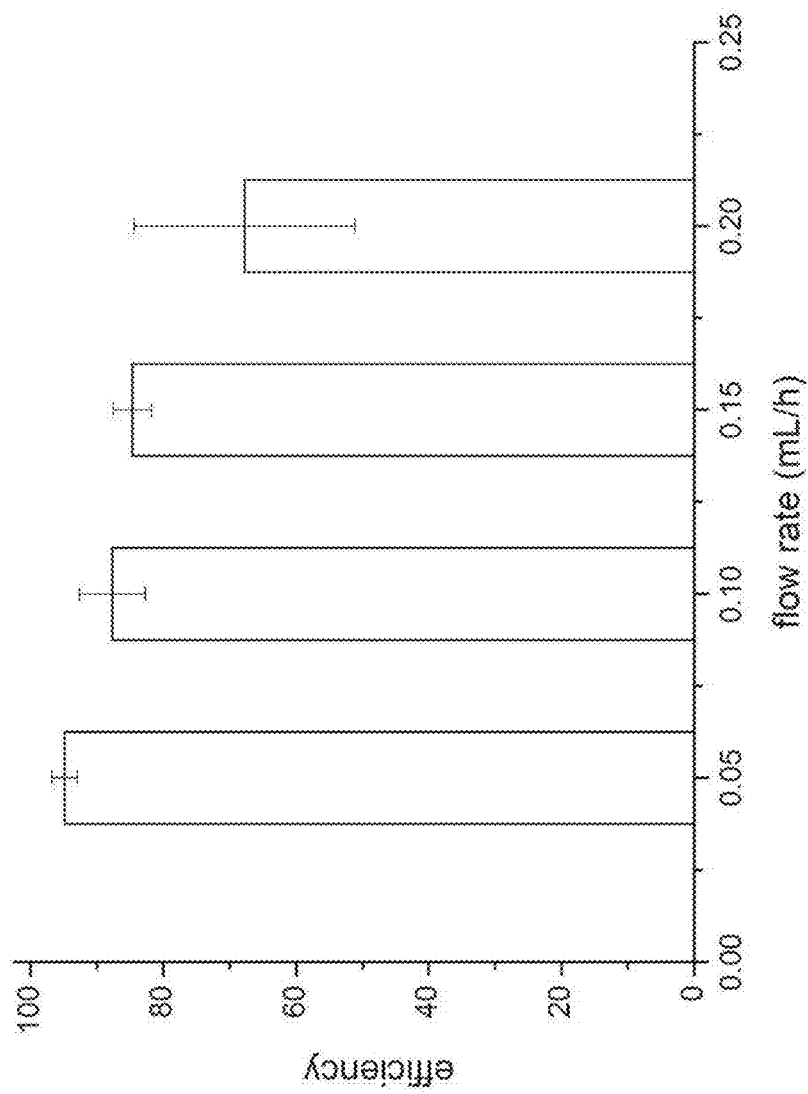
FIG. 8 depicts herringbone channel capture efficiency as a function of flow rate in the chip (bottom).

The overall design of the sepsis chip of the present invention involves two separation regions using anti-CD64 antibodies. The two sections differ by capture efficiency. Capture efficiency can be modulated using flow effects (FIG. 5), antibody concentration (FIG. 6), or by using different types of separation channels to achieve different capture efficiencies. In FIG. 6 antibody concentration (loaded into the chip) shows effects on cell capture. As expected, at high concentrations (>20 μg/mL) the effect of antibody concentration on cell capture decreases. At lower antibody concentrations, the relationship between cell capture and antigen expression is linear (inset), allowing differences in antigen expression to be measured using the chip There may also exist the need to deplete monocytes from the sample prior to CD64 capture (FIG. 7). To maintain high capture efficiency but also aid in optical scanning, herringbone-modified chips used to capture neutrophils after monocyte depletion. Herringbone mixers have been used in cell separations to induce chaotic mixing in the microchannel, increasing interaction between cells and the capture surface. Herringbone sections have high capture efficiency (FIG. 8) and it is demonstrated that antigen expression can be elucidated using these chips. The herringbone chips have greater capture efficiency at higher flow rates than normal, straight channels. For the present invention herringbone regions are used after the 3D depletion section chips as an alternate strategy to increase capture efficiency.

FIG. 7 provides two alternating orientations of the system of the present invention for separating active and resting neutrophils. In FIG. 7A monocytes are depleted (optional) from the blood sample, which is then split into two streams of differing CD64 capture efficiency. A control valve allows captured neutrophils to be eluted for automated counting. FIG. 7B, the two anti-CD64 channels are operated in series (detection occurs after each section). The monocyte depletion sections (first separation region) can be either a 3D chip, herringbone, or combination of the two. The FIG. 7(A) orientation 701 provides a parallel chip orientation wherein both resting 703 and active 704 cells are detecting utilizing a simultaneous exposure to antibody samples for the alternative channels. An inlet 712 introduces the sample through a separation channel 705 which comprises an anti-CD14 surface. A control valve 702 further allows for flow modulation if desired. On the parallel chip 701, active neutrophils 704 and resting neutrophils 703 are exposed to antibody samples, such as anti-CD64, allowing for capture and enumeration. The FIG. 7(B) orientation shows a series-based chip 706, providing for the antibodies to be exposed to both active 709 and resting 710 cell states in serial fashion rather than simultaneously. An inlet 712 introduces a sample into the separation channel 707 which comprises an anti-CD14 surface. A control valve 708 further allows for flow modulation if desired. The series configuration passes the sample through a first zone 709 capable of removing active neutrophils, while the second zone 710 provides for capture of resting neutrophils. With either configuration 701, 706 the enumeration of the captured and resting neutrophils will provide determination of the presence of infection.

Figure 9:
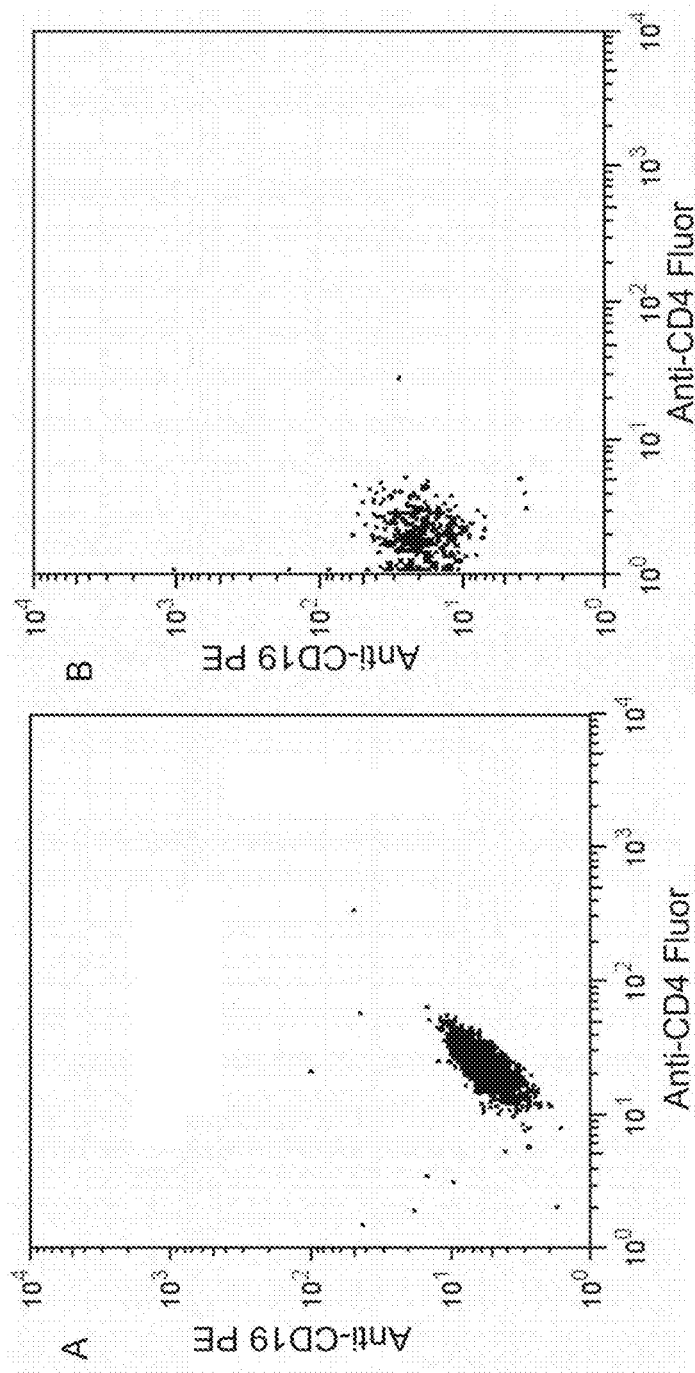
FIG. 9 depicts isolation of CD4+(A) and CD19+(B) cells from lysed blood used tandem cell affinity columns.
Figure 10:
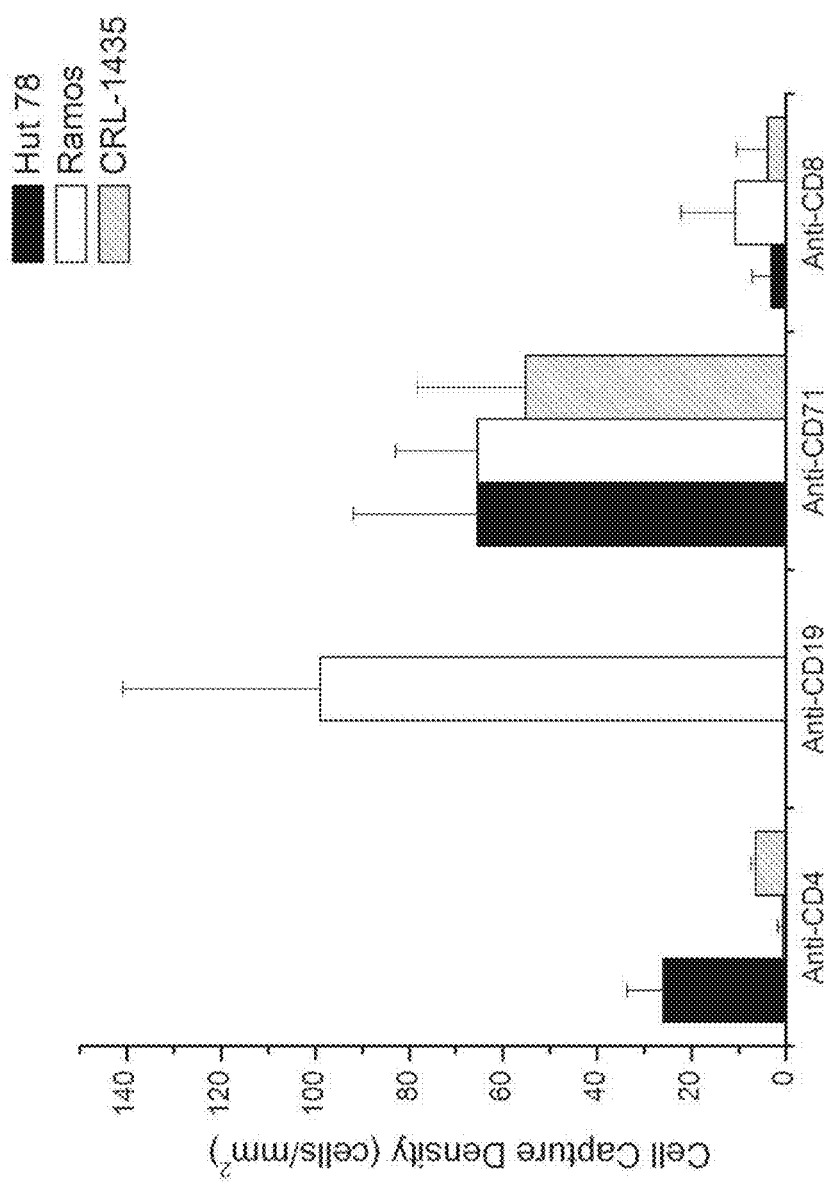
FIG. 10 depicts multi-parameter analysis of a cell mixture using 4 serial affinity regions.

With previous work in cell separations, CD4+ and CD19+ cells were isolated from blood using two open-tubular affinity columns connected in series (see FIG. 9). The purity of CD4+ leukocytes was 87% with 0.2% of captured cells CD19+. The purity of the CD19+ lymphocytes was 82% with 0.1% of the captured cells measured as CD4+. It is therefore possible to use a series approach to remove one cell type before the second cell type is separated. Therefore in one embodiment, depletion zones remove monocytes prior to CD64+ neutrophil isolation. This approach is capable of capturing multiple cell types in a chip, as shown in FIG. 10. In FIG. 10, a chip with four separation regions in series was used on a mixture of HuT 78, Ramos, and CRL-1435 cell lines. The chip contained multiple affinity regions using valves to control surface coating. As expected, the anti-CD4 region captured HuT 78 cells with a small degree of nonspecific binding, while the anti-CD19 region captured Ramos cells with no nonspecific binding. All three of the cell lines express CD71 and were captured on the anti-CD71 region. An anti-CD8 region was used to evaluate nonspecific binding in this case, as none of the cell lines express CD8.

Figure 11:
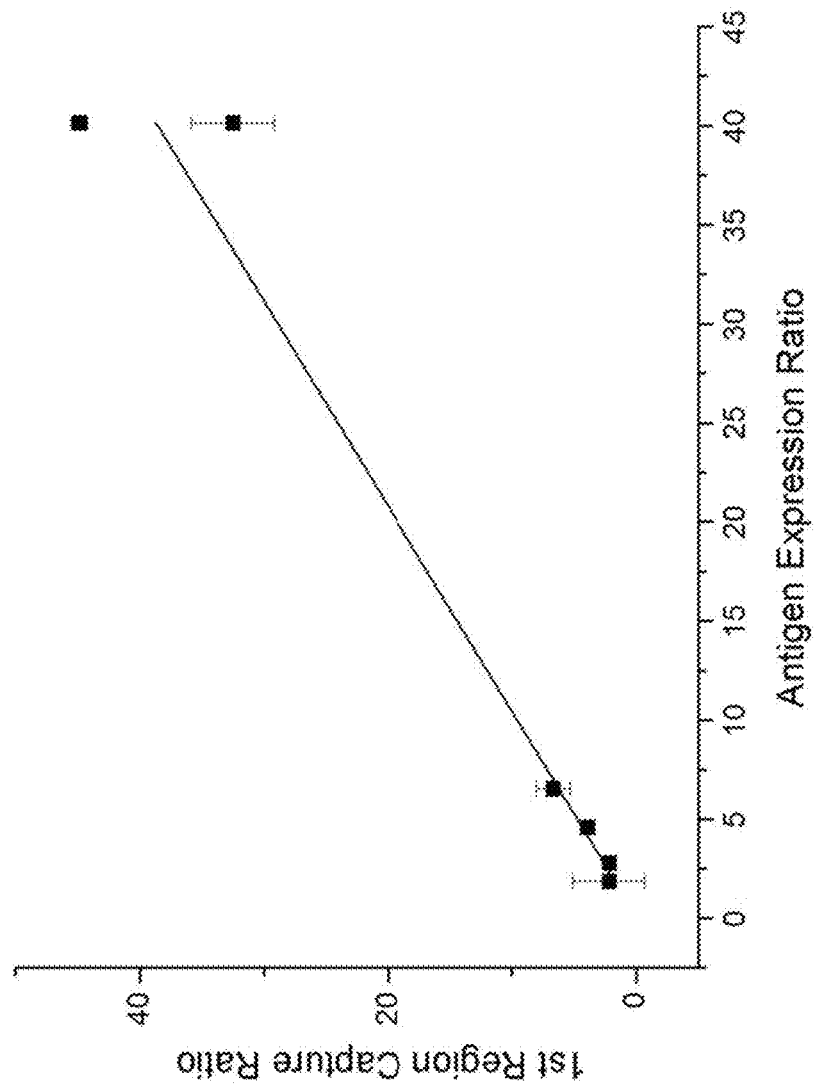
FIG. 11 depicts control of cell capture efficiency by controlling antibody concentration.

Additionally, cell capture may be modulated by varying the antibody concentrations on a chip. In FIG. 11, the effect of antibody concentration in a serial herringbone separation chip is shown with two affinity regions. Control of cell capture efficiency by controlling antibody concentration. A herringbone chip was used to capture CD71+ Ramos cells spiked into blood. The Ramos cell CD71 expression ranged between 3-40 times higher than CD71+ leukocytes in blood. The capture ratio of Ramos cells to CD71+ leukocytes was measured in the chip, with a linear relationship between the cell capture and the antigen expression (y=0.95X−0.11, R2=0.95). As the CD71+ expression increased in Ramos cells (conducted on different days with the same blood samples) the ratio of Ramos:Leukocytes in the chip increased linearly. These results demonstrate that the chips can measure changes in antigen expression and are capable of processing complex samples, such as blood. The first region has a lower concentration of anti-CD19 to serve as a low-efficiency capture region and the second region has a higher anti-CD19 concentration. The ratio of cell capture was calculated as the cell counts in the second region (high efficiency capture) divided by the cell counts in the lowest antibody concentration capture region. It was therefore possible to control the cell capture by changing the antibody concentrations at a single flow rate. This approach simplifies chip design and operation. The range of antigen expression between two cell lines capture in the device was 3- to 40-fold. Since it is expected for neutrophil CD64 expression to increase 10-20× during sepsis, the present invention is then able to generate two affinity regions capable of separating active and resting neutrophils.

In another exemplary embodiment of the present invention, an affinity surface is generated using sandwich approach commonly used for cell separations. The surface is first coated with biotinylated BSA, followed by a layer of neutravidin. A biotinylated antibody is then added to complete the surface coating. This approach allows any biotinylated capture molecule to be used for chip separations. These surfaces are stable under refrigerated, dry storage, and can be functionalized with the final antibody layer in minutes before use, or stored with the antibody for weeks at 4° C.

Cell separations may be conducted using either stop-flow or continuous-flow strategies. In stop flow, the chip is filled with lysed or whole blood, and cells are allowed to settle to the surface for capture. A wash step then removes unbound cells and enumeration occurs. In continuous flow, cells are introduced at a flow rate that ensures low shear force (in the exemplary chips of the present invention, typically 0.05 mL/hr). Sample is continuously introduced in this case, and higher flow rates are used to wash unbound cells prior to cell enumeration. Stop flow methods typically have higher purity, although lower total sample numbers. However, since the objective is capturing neutrophils, with typical concentration ranges of 2,500-6,000 cells/mL, stop flow methods will result in a sufficient number of cells. The absolute neutrophil count is less important than the active/resting neutrophil ratio. In exemplary embodiments, the volume of a single 3D interface section may be around 0.15 mL. Given the range of neutrophils in blood, the number of cells that can be injected into that volume is 2,200-5,400 cells (per 3D section). If the capture efficiency is 55% (an average of previous results, Table 1), then it is expected that 1,100-2,700 cells per section, or 6600-16,000 CD64+ neutrophils for the entire CD64 isolation channel in stop flow mode. In the case of measuring active vs. resting neutrophils, this would represent the total cell count, with the numbers of resting and active cells varying depending on the state of the donor. The number of cells isolated in stop flow will therefore be sufficient for statistical analysis of cell counts. However, if the cell counts are insufficient in stop flow mode, continuous flow can be used to introduce larger total cell volumes. A 20-minute separation would require 30 mL of blood and would inject 75,000-180,000 neutrophils into the chip. Cell lysis requires 1.5 minutes, and washing steps are not necessary. The dye used for image contrast is included in the running buffer, and the scan time to read the entire chip (or several chips at once) is on the order of 30 seconds. The entire analysis time, from sample to answer, is therefore less than 25 minutes. This analysis time is comparable with the staining time when using antibodies and flow cytometry or magnetic separations for CD64 neutrophil counting.

Once modeling reveals the best initial geometries, high-efficiency channels can be used for both the capture of CD64+ resting neutrophils and also to deplete monocytes from blood prior to neutrophil analysis. In both cases, the highest cell capture possible is desired. Since the cell mixture plays a role in the reproducibility, inter-chip variation studies are further conducted with the same sample mixture on the same day.

The lower-efficiency anti-CD64 region will be optimized to capture neutrophils that are activated and have higher CD64 expression. In addition to herringbone channels, chip efficiency may be altered to capture resting and active neutrophils differently. In one embodiment an unmodified channel with an anti-CD64 surface captures activated neutrophils, while a herringbone approach is needed to capture resting neutrophils. In another embodiment the flow rate of the chip is altered to increase or decrease capture efficiency. One way to alter the flow rate is to change the channel dimensions, but this approach may also change capture efficiency in unforeseen ways. In an exemplary embodiment, in order to optimize chip designs, commercially available beads are utilized with known differences in antigen density. These antigen-density beads are commonly used in flow cytometry as standards to measure antigen expression. Beads with antigen densities are used matching the densities of CD64 on activated and resting neutrophils. This approach allows chip designs to be optimized in a controlled system. In cell capture chips, the height of the channels is critical, and the length (along the flow direction) is also important. Of less impact on capture performance is the width of the channel, and this dimension can be reduced to increase the linear flow rate of this chip section. Using this approach, faster moving cells will have less interaction time and cell capture efficiency will decrease. The channel width may be optimized so that >90% capture of activated high antigen density beads is observed while minimizing capture of lower antigen density beads to <10%. Given the differences in CD64 expression between activated and resting neutrophils, this difference in capture efficiency is feasible. Cells that exit the narrow anti-CD64 section will then enter another anti-CD64 that has channels that are similar in dimension to the anti-CD14 region. The restoration of a slower linear flow rate will increase capture efficiency so that lower antigen density cells or beads are captured.

The above embodiments may exist as alternate approaches or in combination with the multiple fluidic architectures presented for efficient cell separations. While there may be preferable single approach, it is also possible that the present invention combines different channel designs in the same chip.

In addressing sepsis models, in one embodiment the present invention is designed to deplete monocytes prior to CD64+ neutrophil using blood samples. Commercial sources of blood are utilized to validate monocyte depletion and neutrophil capture. Determined are the necessary flow rates, sample volumes, and analysis times as well as antibody coating required for neutrophil capture. Currently flow cytometry is the standard method for such an analysis, using several fluorescent antibody labels to identify cells. However, any newly developed methods that could simplify such analysis and reduce the cost of measurement would be applicable on sepsis assays for point of care diagnosis. Affinity methods to date have run into interferences from cells that also express CD64, such as monocytes. It is possible to use magnetic beads or differential shear force to remove cells, however this approach is imprecise. In one embodiment, first-stage cell separation units comprising a plurality of separation channels, which may be 3D, or a combination of herringbone mixers or micropillars, and the like, are utilized to deplete interfering cells so that a subsequent separation stage can isolate target cells for analysis. This approach is based on tandem separations. The first zone will operate under the principle of negative selection, capturing monocytes and preventing them from entering subsequent separation regions.

In an exemplary embodiment of the present invention regarding blood sample preparation, standardized blood samples available from commercial sources are not identified in any way or linked to donors. The benefit of using such blood samples is that they are analyzed beforehand and have certified concentrations of all major blood cell types. CD14+ monocyte depletion in lysed and whole blood is then tested. Lysis protocols are implemented using deionized water or $NH_4Cl$-based buffers, followed by a saline buffer to restore proper salinity to leukocytes. To assess the influence of erythrocytes on our chip separations, chips of the present invention are coated with anti-CD14 to deplete monocytes. The same blood sample is utilized for all chip designs, which compare CD14+ monocyte concentrations in the chip effluent using flow cytometry and fluorescence microscopy. Monocytes are stained with anti-CD14 Alexa Fluor 647 for identification. By measuring cells that pass through the chip, the capture efficiency in whole and lysed blood is determined. For lysed blood, leukocytes are centrifuged and re-suspended at the same concentration as in the original blood, in order to eliminate concentration effects on cell capture. In this manner, the effects of erythrocytes are compared to blood viscosity to lysed blood samples on cell capture. It is anticipated that if whole blood does not yield sufficient performance (>90% capture efficiency of CD14+ lymphocytes), then lysed blood would be used in future protocols.

To assess monocyte depletion, chips with only one separation section coated with anti-CD14 are used. The effluent of these chips will be analyzed to determine cell depletion. For exemplary purposes, both the capture efficiency of monocytes as well as the capture capacity are measured. The total number of monocytes anticipated in a standard sample of blood (30 mL) is on the order of 8000 cells in the chip. Each 3D section for monocyte depletion can capture a theoretical maximum of 2200 cells, based on surface coverage, which can approach 100% (see FIG. 2). Therefore six 3D sections in series captures all monocytes in the blood sample. The capacity for monocyte measurement does not need to be excessively high, but the capture efficiency should be high and the nonspecific binding low. CD64+/CD14+ monocyte concentrations before separation and after elution from the anti-CD14 are measured, as well as capture capacity by monitoring the monocyte population eluting from the chip over time. A sharp increase in the rate of monocytes exiting the chip will signal that the affinity surface is saturated (see FIG. 4). The separation channel is also monitored using light microscopy in real time, to observe cell capture effects. In designing the chip, the most important criteria will be the capture efficiency. However, the rate of nonspecific binding must also be low. CD64+ neutrophil capture should be preferably 0.1% or less.

One issue with blood measurements of any kind is the presence of erythrocytes at higher numbers than leukocytes. However, a lysis protocol can be used to preserve leukocytes while removing erythrocytes prior to analysis. It is shown repeatedly in literature that the remaining fragments of erythrocytes do not impede cell separation. The other issue is nonspecific binding in the CD14 and CD64 capture channels. The present invention is capable of separating blood cells with 97-99% purity, and with enhanced separation efficiency the accuracy thus improves.

Figure 12:
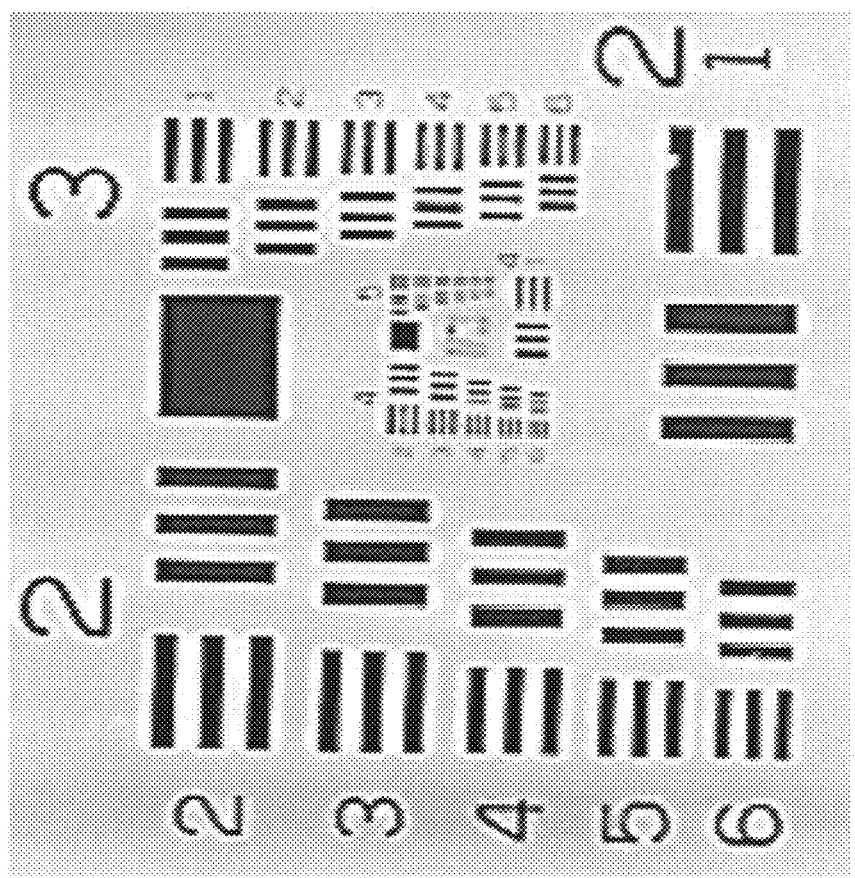
FIG. 12 depicts USAF 1951 Resolution Bar Target image obtained using a desktop flatbed scanner at 2400×2400 DPI resolution.

In another embodiment of the present invention, the chip configuration eliminates the need to manually count cells or image them via microscopy. The cells are counted in the chip after the sample has been introduced, using flatbed scanner technology generally available. In order to count cells in the chip, a contrast dye is added to the running buffer that will stain all cells for bright field or fluorescence imaging. Labeling all cells has an inherently high signal-to-noise ratio when compared to immunofluorescence. The automated system will aid in translation of the present invention to the clinical lab use. Optical scanning using a flatbed scanner allows for microfluidic chips to be imaged inexpensively in a user-friendly format. Optical scanner resolution for an inexpensive ($250-$300) desktop scanner often exceeds 2400×2400 dots per inch (DPI), with higher resolution possible using interpolative scanning. The preliminary image in FIG. 12 shows a USAF resolution target scanned with a 2400×2400 DPI desktop scanner. The system resolves features that are 16 mm apart (2400×2400 interpolation). Given the scale of cells imaged in the system of the present invention (10-15 mm), modern scanning systems are able to resolve cells in the chip. The 5,1 element was resolved, yielding a spatial resolution of 16 μm. This preliminary result shows that an inexpensive scanning system has spatial resolution approaching single cells.

FIG. 13 shows the scanning, or enumeration, action of the present invention. For the present invention two approaches that can be used for optical scanning of cells, depending on the dye used to stain cells for contrast. In FIG. 13A, a dark-contrast dye stains all cells 1303 and the chip is read out using reflectance as the scanner 1300 progresses 1301 across the separation channel (referred to also as an optical channel). The scanner head 1300 provides the light source and detector in this case. This approach requires minimal/no hardware modification. As presented herein, a desktop scanner approaches single cell resolution. In FIG. 13B, a bank of LEDs 1307 (only 1 is shown for clarity) illuminates the chip from above. All cells 1304 in this case are stained with a fluorescent dye such as Hoechst 33342 and the chip is imaged 1305. A thin film 1306 under the chip blocks excitation light, so that only fluorescence light is measured. The cells can be counted individual or an aggregate signal can be measured. If bright field imaging is used, it is feasible to utilize the standard reflected light optical scanning approach that is traditionally used in flatbed scanners. This approach requires no hardware modification. The benefit of using this approach is that any scanner with sufficient resolution and contrast may be used. In addition, since the scan area of most scanners is 8×11" or 11×17" multiple chips may be imaged at once if needed. For fluorescence imaging, an array of LEDs is placed above the chip to illuminate the device uniformly. A dye stains all cells and fluorescence is imaged through a thin film filter to block the LED illumination. This approach has higher signal to noise than reflectance imaging. The LED module is configured to house a chip, and can then be placed on any suitable scanner for imaging. For exemplary purposes, the spatial resolution and contrast is evaluated using USAF 1951 Resolution Bar Targets and USAF Contrast targets for both approaches.

In an exemplary embodiment, the contrast dye will be added to the running buffer during the separation. Hoechst 33342 is an example dye that will stain all cell nuclei for counting, but will not contribute significant background fluorescence. For bright field imaging, Nile Blue derivatives can be detected either by bright field or fluorescence. To optimize and calibrate our system, cells of known concentration are loaded into the chip and counted via standard microscopy. Counting may then be performed with IMAGEJ software and a custom plugin. Actual cell counts are compared with the aggregated signal (i.e. total fluorescence or dye), to see which approach is most accurate. The latter will reduce the optical resolution required, but may be less accurate than counting cells directly. The software tabulates the total cell counts from each affinity region and will provide the ratio of cells counted in the active and resting neutrophil regions as well as the total neutrophil count. It is expected that there will be some cross-talk between CD64+ neutrophils, but that the ratio of cells in the two regions will correlate with sepsis.

In addressing sensitivity and spatial resolution of optical scanning of the entire chip, single-cell resolution is possible by using a high-contrast dye in bright field or fluorescence scanning to eliminate the need for high sensitivity, resulting in a simple cell enumeration method that requires no user intervention. Once cells are loaded and separated in the chip, the chip is placed on a flatbed scanner and cells are counted as the entire chip is scanned. The automated enumeration system will help translate the present invention to point of care systems.

Neutrophils have shown an increase in CD64 expression during sepsis. Increased CD64 expression is a direct result of infection, unlike other methods that look at bacterial load. A burn, which increases total neutrophil numbers, will not result in increased CD64 expression unless infection occurs. Therefore CD64 expression can be used as a diagnostic marker for sepsis. Using an anti-CD71 capture channel, a ratio of antigen density between two cell types is equivalent to the ratio of cell capture in the same chip under identical conditions. It is then an embodiment of the present invention to generate channels where cell capture efficiency is modulated by altering antibody concentration on the chip surface. The antibody concentration may be kept constant but generate chip sections with different linear flow rates or capture geometries if needed.

Pursuing optimized chip designs prevents the drawbacks of traditional lab-on-a-chip devices. Those drawbacks include subjective analysis and heavy operator burden (analysis time, functionality of devices, etc.). The automated approach of the present invention will decrease user error and operator burden, and will allow for translation to point of care diagnosis. The cost per device is significantly lower than extant methods such as flow cytometry and procalcitonin assays, and can be implemented in a wider variety of clinical settings. Further, the present invention overcomes problems associated with current cell separation methods, and result in isolation of target cells with high purity. In one embodiment, the present invention provides a neutrophil assay as a relevant marker and assay for sepsis. Using several animal models to control the type of sepsis, the degree of sepsis and septic shock is assayed, allowing for setting quantitative cutoff values to predict sepsis.

It is therefore an embodiment of the present disclosure to provide a system and method for utilizing a microdevice for the rapid detection of an inflammatory response associated with infection which includes the blood stream. In another embodiment the detection rapidly determines the presence of systemic inflammatory response syndrome, or SIRS, also known as sepsis. The present invention includes an in-vitro, diagnostic, point of care device, including a microfluidic channel for conducting patient blood samples for purposes of scanning and/or detection of levels of desired contents, or markers. In one embodiment, the system utilizes cell counts to test for infection and inflammatory response, determining whether the cells of the same phenotype are separated based on whether they are 'active' or 'inactive'.

In a preferred embodiment of the present disclosure, a microdevice separates blood cells obtained from a patient based on differences in antigen expression. Specifically, cells of the same phenotype are separated based on whether or not they are activated during infection or resting. The device of the present disclosure takes a small sample of blood and provides differential cell counts that can be used to test for infection and inflammatory response.

Sepsis and other infection is usually characterized by blood culture, which takes 24-48 hours to identify. Currently, the mortality rate for sepsis is high due to this long waiting period. Identifying sepsis and other infections earlier can increase survival rates by over 10 times. It is another embodiment of the present disclosure to detect the presence of infection in a rapid manner (less than 24 hours). In another embodiment, the presence of infection in the blood sample is determined in less than 12 hours. In yet another embodiment, the presence of infection in the blood sample is determined in less than 8 hours. In yet another embodiment, the presence of infection in the blood sample is determined in less than 6 hours.

In one embodiment a method for determining whether a subject has an infection comprises contacting detectably labeled antibodies specific for CD64 with blood leucocytes in a sample obtained from a patient; forming a measurable amount of CD64-antibody complex; identifying abnormal expression of CD64 on blood leucocytes in a sample obtained from the patient from the amount of CD64-antibody complex; and identifying abnormal expression of the antibody complexes on the blood leucocytes in the sample CD64-antibody complex, wherein abnormal expression of CD64 is indicative of the subject having a bacterial infection. In one embodiment the sample may be whole blood. In another embodiment, the leucocytes are neutrophils. The complexes are then measured to determine the presence of active CD64 antibody complexes. Counting can be implemented using optical scatter, fluorescence detection, electric resistance, electrical impedance, or other means of registering cells on the surface such as wide field bright- or dark-field imaging.

Those skilled in the art will recognize that the methods and systems of the present disclosure may be implemented in many manners and as such are not to be limited by the foregoing exemplary embodiments and examples. In other words, functional elements being performed by single or multiple components, in various combinations of hardware and software or firmware, and individual functions, may be distributed among various software applications at either the client level or server level or both. In this regard, any number of the features of the different embodiments described herein may be combined into single or multiple embodiments, and alternate embodiments having fewer than, or more than, all of the features described herein are possible.

Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features as well as those variations and modifications that may be made to the hardware or software or firmware components described herein as would be understood by those skilled in the art now and hereafter.

Furthermore, the embodiments of methods presented and described as diagrams, schematics or flowcharts in this disclosure (such as the Figures) are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

While various embodiments have been described for purposes of this disclosure, such embodiments should not be deemed to limit the teaching of this disclosure to those embodiments. Various changes and modifications may be made to the elements and operations described above to obtain a result that remains within the scope of the systems and processes described in this disclosure.

| REFERENCES | | |
|---|---|---|
| [1] Patent | U.S. Pat. No. 7,767,395 B2 |
| [2] Patent | U.S. Pat. No. 8,439,835 B1 |
| [3] Patent | U.S. Pat. No. 8,518,648 B2 |
| [4] Patent | U.S. Pat. No. 5,804,370 A |
| [5] Patent App | US 20110059858 A1 |
| [6] Patent | U.S. Pat. No. 8,669,113 B2 |
| [7] Patent | U.S. Pat. No. 8,304,230 B2 |
| [8] Patent | U.S. Pat. No. 8,476,028 B2 |
| [9] Patent | U.S. Pat. No. 7,645,573 B2 |
| [10] Patent App | US 20080114576 A1 |

What is claimed is:

1. A method of identifying the presence of infection, comprising:
   a. flowing a patient sample through a microfluidic device having a substrate having formed therein one or more separation channels, at least one portion of the one or more separation channels having a plurality of monolayers, wherein at least a portion of said monolayers comprises a monocyte affinity surface capable of monocyte cell capture, and one or more optical zones having a plurality of monolayers, wherein at least a portion of said monolayers comprises a neutrophil affinity surface capable of neutrophil cell capture;
   b. capturing active neutrophils in at least one separation channel wherein at least a portion of said monolayers in the at least one separation channel comprises a neutrophil affinity surface capable of capturing the active neutrophils;
   c. capturing resting neutrophils in at least one separation channel wherein at least a portion of said monolayers in the at least one separation channel comprises a neutrophil affinity surface capable of capturing the resting neutrophils;
   d. enumerating the active and resting neutrophils in the optical zone; and
   e. determining the ratio of active-to-resting neutrophils to thereby identify the presence of infection.

2. The method of claim 1, further comprising depleting monocytes from the sample in the separation channels prior to neutrophil capture.

3. The method of claim 1, wherein the plurality of separation channels have more than one monocyte affinity surfaces capable of cell capture of more than one monocytes.

4. The method of claim 1, further comprising enumerating the active and resting neutrophils using an optical scanner.

5. The method of claim 4, further utilizing a high-contrast dye in bright field.

6. The method of claim 4, further utilizing fluorescence scanning.

* * * * *